(12) United States Patent
Chen

(10) Patent No.: US 6,201,329 B1
(45) Date of Patent: Mar. 13, 2001

(54) PUMP HAVING MAGNETIC BEARING FOR PUMPING BLOOD AND THE LIKE

(75) Inventor: H. Ming Chen, Latham, NY (US)

(73) Assignee: Mohawk Innovative Technology, Inc., Albany, NY (US)

( * ) Notice: Subject to any disclaimer, the term of this patent is extended or adjusted under 35 U.S.C. 154(b) by 0 days.

(21) Appl. No.: 09/046,334

(22) Filed: Mar. 23, 1998

Related U.S. Application Data
(60) Provisional application No. 60/063,337, filed on Oct. 27, 1997.

(51) Int. Cl.[7] .............................. H02K 7/09; F16C 32/04; F16C 39/06
(52) U.S. Cl. .................. 310/90.5; 417/423.7; 417/423.1; 600/16; 623/3
(58) Field of Search ........................ 310/90.5, 51, 68 B, 310/103, 209, 191; 623/3; 417/423.1, 423.7; 600/16

(56) References Cited

U.S. PATENT DOCUMENTS

| | | | |
|---|---|---|---|
| 3,747,998 | * 7/1973 | Klein et al. | 308/10 |
| 4,211,452 | * 7/1980 | Poubeau | 308/10 |
| 4,268,095 | 5/1981 | Millner | 310/90.5 |
| 4,779,614 | 10/1988 | Moise | 600/16 |
| 5,055,005 | 10/1991 | Kletschka | 417/356 |
| 5,084,643 | 1/1992 | Chen | 310/90.5 |
| 5,133,527 | 7/1992 | Chen et al. | 348/550 |
| 5,158,440 | 10/1992 | Cooper et al. | 417/423.1 |
| 5,175,457 | 12/1992 | Vincent | 310/15 |
| 5,195,877 | 3/1993 | Kletschka | 417/356 |
| 5,202,824 | 4/1993 | Chen | 364/508 |
| 5,205,384 | 4/1993 | Heshmat | 188/264 B |
| 5,216,308 | * 6/1993 | Meeks | 310/90.5 |
| 5,220,232 | 6/1993 | Rigney, II et al. | 310/90.5 |
| 5,248,239 | * 9/1993 | Andrews | 415/104 |
| 5,270,601 | 12/1993 | Rigney, II | 310/90.5 |
| 5,326,344 | 7/1994 | Bramm et al. | 623/3 |

(List continued on next page.)

FOREIGN PATENT DOCUMENTS

| | | | |
|---|---|---|---|
| 57-173606 | * 10/1982 | (JP) | 310/90.5 |
| WO94/06486 | * 3/1994 | (WO) | 623/3 |

OTHER PUBLICATIONS

"Physics", O'Hanian, pp. 728, 1985.*
M. Marinescu et al, "A New Improved Method for Computation of Radial Stiffness of Permanent Magnet Bearings," *IEEE Transactions on Mechanics,* vol. 30(5), Sep., 1994, pp. 3491–3494.
C. Henrikson et al, "Magnetically Suspended Momentum Wheels for Spacecraft Stabilization," AIAA Paper No. 74–128, AIAA 12th Aerospace Sciences Meeting, Washington, DC, Jan. 30–Feb. 1, 1994, pp. 1–8.

(List continued on next page.)

*Primary Examiner*—Karl I Tamai
(74) *Attorney, Agent, or Firm*—James C. Simmons

(57) ABSTRACT

In order to provide a blood pump bearing having a suitable stiffness, magnetic rings for a journal bearing are provided on each of the stationary portion and the rotor and disposed in magnetically interacting facing relationship on opposite sides of a gap, and a thrust bearing is provided on the stationary portion and the rotor and disposed with magnets in magnetically interacting facing relationship on opposite sides of the same or another gap. The pump motor preferably has a bearing span which is at least about 2½ times greater than an average radius of the distributed magnetic force. In accordance with one embodiment, the stator has at least one axial extension, an axially extending gap is provided between the stator and rotor, and a journal bearing has magnets interactively disposed on opposite sides of the gap. In accordance with another embodiment, at least one pair of permanent magnets on the housing are movable relative to at least one pair of permanent magnets on the rotor which are oriented in an attractive relationship thereto in response to axial displacement of the rotor.

26 Claims, 8 Drawing Sheets

U.S. PATENT DOCUMENTS

| | | | |
|---|---|---|---|
| 5,385,581 | 1/1995 | Bramm et al. | 623/3 |
| 5,443,503 | 8/1995 | Yamane | 623/3 |
| 5,457,086 | 10/1995 | Rigney, II | 310/90.5 |
| 5,521,448 | 5/1996 | Tecza et al. | 310/90.5 |
| 5,561,335 * | 10/1996 | Dunfield et al. | 310/90.5 |
| 5,601,418 | 2/1997 | Ohara et al. | 417/420 |
| 5,652,473 * | 7/1997 | Delamare et al. | 310/90.5 |
| 5,666,014 | 9/1997 | Chen | 310/90.5 |
| 5,804,899 * | 9/1998 | Jamain et al. | 310/90.5 |
| 5,840,070 * | 11/1998 | Wampler | 604/131 |
| 6,105,272 * | 1/2000 | Antaki et al. | 417/356 |

OTHER PUBLICATIONS

P. Allaire et al, "Prototype Continuous Flow Ventricular Assist Device Supported on Magnetic Bearings," *Artificial Organs*, vol. 20(6), 1966, pp. 582–590.

R. Hart et al, "A Magnetically Suspended and Hydrostatically Stabilized Centrifugal Blood Pump," *Artificial Organs*, vol. 20(6), 1966, pp. 591–596.

K. Nishimura et al, "Development of a Magnetically Suspended Centrifugal Pump as a Cardiac Assist Device for Long–Term Application," *ASAIO Journal*, 1996, vol. 42, pp. 68–71.

J. Yonnet, "Permanent Magnet Bearings and Couplings," *IEEE Transactions on Magnetics*, vol. Mag–17(1), Jan., 1981, pp. 1169–1173.

H. Chen, "Design and Analysis of a Sensorless Magnetic Damper," paper presented at the International Gas Turbine and Aero engine Congress & Exposition, Houston, TX, Jun. 5–8, 1995.

K. Qian et al, "Chronic Left Ventricular Assist in Calves with a Pulsatile Impeller Pump," *ASAIO Journal*, 1997, vol. 43, pp. 89–91.

G. Bearnson et al, "Development of a Prototype Suspended Rotor Ventricular Assist Device," *ASAIO Journal*, 1996, vol. 42, pp. 275–281.

G. Bearnson et al, "Pulsatile Operation of a Centrifugal Ventricular Assist Device with Magnetic Bearings," *ASAIO Journal*, 1996, vol. 42, pp. M–620–M–624.

K. Qian et al, "A Superconductive Electromagnetic Pump Without Any Mechanical Moving Parts," *ASAIO Journal*, 1993, vol. 39, pp. M649–M653.

Y. Taenaka et al, "Chronic Evaluation of a Compact Nonseal Magnet Pump as a Nonpulsatile Pump for Long–Term Use," *ASAIO Transactions*, vol. 37, 1991, pp. M243–M245.

S. Phillips et al, "Using Magno Strictive Metal as a Pump for Biomedical Application," *ASAIO Transactions*, vol. 37, 1991, pp M509–M510.

T. Nakazawa et al, "Hydraulic Assessment of the Floating Impeller Phenomena in a Centrifugal Pump," *Artificial Organs*, vol. 21(1), 1997, pp. 78–82.

C. Park et al, "A New Magnetically Suspended Centrifugal Pump: In Vitro and Preliminary In Vivo Assessment," *Artificial Organs*, vol. 20(2), 1996, pp. 128–131.

Y. Taenaka et al, "Development of a Centrifugal Pump with Improved Antithrombogenicity and Hemolytic Property for Chronic Circulatory Support," *Artificial Organs*, vol. 20(6), 1996, pp. 491–496.

R. Jarvik, "System Considerations Favoring Rotary Artificial Hearts with Blood–Immersed Bearings," *Artificial Organs*, vol. 19(7), 1995, pp. 565–570.

N. Mendler et al, "Seal–less Centrifugal Blood Pump with Magnetically Suspended Rotor: Rot–a–flot," *Artificial Organs*, vol. 19(7), 1995, pp 620–624.

D. Dame, "A Teaspoon Pump for Pumping Blood with High Hydraulic Efficiency and Low Hemolysis Potential," *Artificial Organs*, vol. 20(6), 1996, pp 613–617.

T. Yamane et al., "Design of a Centrifugal Blood Pump with Magnetic Suspension," *Artificial Organs*, vol. 19(7), 1995, pp. 625–630.

T. Yamane et al, "New Mechanism to Reduce the Size of the Monopivot Magnetic Suspension Blood Pump: Direct Drive Mechanism," *Artificial Organs*, vol. 21(7), 1997, pp 620–624.

T. Yamada et al, "Chronic Animal Experiment with Magnetically Suspended Centrifugal Pump," *Artificial Organs*, vol. 21(7), 1997, pp 635–638.

R. Kung et al, "Design Considerations for Bearingless Rotary Pumps," *Artificial Organs*, vol. 21(7). 1997, pp. 645–650.

K. Qian et al, "Realization of a Permanent Implantable Pulsatile Impeller Heart with Magnetically Suspended Motor," *Artificial Organs*, vol. 21(7), 1997, pp 670–674.

M. Sueshiro et al, "Trial Manufacture of Eccentric Roller Type Total Artificial Heart," *Artificial Organs*, vol. 21(7), 1997, pp 735–738.

Y. Okada et al, "Magnetically Levitated Motor for Rotary Blood Pumps," *Artificial Organs*, vol. 21(7), 1997, pp 739–745.

S. Naganuma et al, "Development of a Novel Centrifugal Pump: Magnetic Rotary Pump," *Artificial Organs*, vol. 21(7), 1997, pp 746–750.

T. Tsukiya et al, "Visualization of the Flow Patterns in the Magnetically Suspended Centrifugal Blood Pump," Abstract No. 173, *Artificial Organs*, vol. 21(6), 1997, p 518.

P. Allaire et al, "Continuous Flow Magnetically Suspended Centrifugal Pump Ventricular Assist Device (CFVAD III): Design and Testing," Abstract 139, Artificial Organs 21(6), 1997, p. 510.

H. Kim et al, "In Vitro Characterization of a Magnetically Suspended Continuous Flow Ventricular Assist Device," *ASAIO Journal*, vol. 41, 1995, pp. M359–M364.

P. Khanwilkar et al, "Using Hybrid Magnetic Bearings to Completely Suspend the Impeller of a Ventricular Assist Device," *Artificial Organs*, vol. 20(6), 1966, pp. 597–604.

C. Park et al, "A Magnetically Suspended Centrifugal Pump—In Vitro and In Vivo Assessment," *ASAIO Journal*, vol. 41, 1995, pp M345–M350.

H. Chen et al, Paper "Novel Magnetic Bearings for a Flywheel Energy Storage System," Paper Given at Pacific Center of Thermal–Fluids Engineering, Honolulu, Hawaii, ISROMAC–6, 1996.

K. Oka et al, "Magnetic Suspension System with Permanent Magnet Motion Control," Paper Given at Fourth International Symposium on Magnetic Bearings, ETH Zurich, Aug., 1994.

F. Dorman et al, "Progress in the Design of a Centrifugal Cardiac Assist Pump with Trans–cutaneous Energy Transmission by Magnetic Coupling," *Trans. Amer. Soc. Artif. Int. Organs*, vol. 15, 1969, pp. 441–448.

* cited by examiner

PUMP HAVING MAGNETIC BEARING FOR PUMPING BLOOD AND THE LIKE

Priority of U.S. provisional application serial no. 60/063,337, filed Oct. 27, 1997, which is hereby incorporated herein by reference, is hereby claimed.

The present invention relates generally to magnetic bearings for pumps such as, for example, blood pumps implanted in the human body to assist blood flow.

References (in addition to those cited hereinafter) which may be of interest in the development of magnetic bearings include my U.S. Pat. Nos. 5,084,643; 5,133,527 (with others); 5,202,824; and 5,666,014; U.S. Pat. Nos. 5,175,457 and 5,521,448, which above patents are hereby incorporated herein by reference; M. Marinescu et al, "A New Improved Method for Computation of Radial Stiffness of Permanent Magnet Bearings," *IEEE Transactions on Magnetics*, vol. 20, no. 5, September, 1994, pp 3491–3494; and C. Henrikson et al, "Magnetically Suspended Momentum Wheels for Spacecraft Stabilization," AIAA paper no. 74-128, AIAA $12^{th}$ Aerospace Sciences Meeting, Washington, D.C., Jan. 30–Feb. 1, 1974.

A major limitation of continuous flow blood pumps utilizing conventional (non-magnetic) bearings is the seal required for separating the blood from the bearing and the lubricant. Seals fail mechanically or by the build-up of amorphous material at the rotating and non-rotating interface.

While various blood lubricated supports such as conventional hydrodynamic bearings and sapphire jewel bearings have been proposed, deposition and homolysis in the interface due to frictional heat and shear stress may nevertheless be excessive.

Relative movement between parts of mechanical bearings or high sheer stresses or friction at interfaces of impellers with glands may cause blood cells to undesirably rupture.

Magnetic suspension of the rotor has been proposed as a suitable bearing means for a blood pump. In such a pump, blood may flow between the stator and rotor since the rotor is suspended relative to the stator. It is considered desirable to have a path through such a pump for free flow of blood so that it does not undesirably stagnate and thus coagulate and which path is large enough to prevent shearing of individual blood cells.

One magnetic suspension concept for blood pump bearings utilizes five actively controlled bearing axes. See P. Allair et al, "Prototype Continuous Flow Ventricular Assist Device Supported on Magnetic Bearings," *Artificial Organs*, vol. 20, no. 6, 1996, pp 582–590. Such a suspension system is mechanically and electrically complex and consumes much power. Another suspension concept utilizes four active radial axes, and still another utilizes four active axial electromagnets. See R. Hart et al, "A Magnetically Suspended and Hydrostatically Stabilized Centrifugal Blood Pump," *Artificial Organs*, vol. 20, no. 6, 1996, pp 591–596; and K. Nishimura et al, "Development of a Magnetically Suspended Centrifugal Pump as a cardiac Assist Device for Long-Term Application," *ASAIO Journal*, 1996, pp 68–71, respectively. These systems are still electrically complicated.

U.S. Pat. Nos. 4,944,748; 5,078,741; and 5,385,581 to Bramm et al disclose a magnetically suspended and rotated rotor for a blood pump which is supported by permanent magnets on the impeller and pump housing at each end of the pump to provide two passive journal or radial bearings, and the axial position stabilized by an electromagnetic on each end of the pump housing which interact with the permanent magnets on the impeller respectively to provide an actively controlled thrust bearing. The permanent magnets and electromagnets on the pump housing are radially spaced across a gap between the pump housing and the impeller from the impeller magnets respectively.

The radial and thrust bearings of the Bramm et al pump appear to be very soft while inefficiently using a lot of permanent magnetic material. In this regard, it has been suggested that a permanent magnet bearing stiffness is proportional to the permanent magnet cross-sectional area squared but inversely proportional to the fourth power of the average distance between the two magnets. See J. Yonnet, "Permanent Magnet Bearings and Coupling," *IEEE Transactions on Magnetics*, vol. Mag-17, no. 1, January, 1981. Judging from the pump configuration, it is believed that this distance would have to be 0.5 inch or more thereby providing very soft radial bearings. Since the pump rotor of the Bramm et al patents may be super-critical (operating above a critical speed), slight shock load may cause the Bramm et al rotor to undesirably undergo large lateral excursions due to the bearing softness and lack of damping. The Bramm et al thrust bearing does not appear to be stiff or electrically efficient. The make-up of Bramm et al's axial sensor of infrared diodes and photo receivers is an indication of such thrust bearing softness due to its lacking sensing resolution or accuracy. It is also believed that the Bramm et al motor may be of the induction type which would not be electrically efficient due to the large gaps between the rotor and stator.

It is accordingly an object of the present invention to provide blood pump bearings which are suitably stiff.

It is another object of the present invention to provide blood pump bearings which will not damage the blood cells.

It is still another object of the present invention to provide blood pump bearings which are efficient (require little power consumption).

It is a further object of the present invention to provide blood pump bearings which are rugged, dependable, and maintenance-free.

It is yet another object of the present invention to provide blood pump bearings which are non-complicated and inexpensive.

In order to provide such blood pump bearings wherein a suitable stiffness may be obtained, in accordance with the present invention, at least one radially extending gap is provided between a stationary portion of the pump and the rotor, magnetic means for a journal bearing are provided on each of the stationary portion and the rotor and disposed in interacting facing relationship on opposite sides of at least one of the at least one gap, and magnetic means for a thrust bearing are provided on each of the stationary portion and the rotor and disposed in interacting facing relationship on opposite sides of at least one of the at least one gap.

Also in order to provide such bearings, in accordance with the present invention, the pump motor has a bearing span which is at least about 2½ times greater than an average radius of the distributed magnetic force.

Also in order to provide such bearings, in accordance with the present invention, the stator has at least one axial extension, an axially extending gap is provided between the stator and rotor, and interactive magnetic means for a journal bearing are disposed on opposite sides of the gap.

In order to provide such a blood pump thrust bearing, in accordance with the present invention, the thrust bearing comprises means responsive to axial displacement of the rotor for moving at least one pair of permanent magnets on the stator relative to at least one pair of permanent magnets on the rotor which are oriented in an attractive relationship thereto.

The above and other objects, features, and advantages of the present invention will be apparent in the following detailed description of a preferred embodiment thereof when read in conjunction with the accompanying drawings wherein the same reference numeral will denote the same or similar parts throughtout the several views.

DETAILED DESCRIPTION OF A PREFERRED EMBODIMENT

Figure 1:
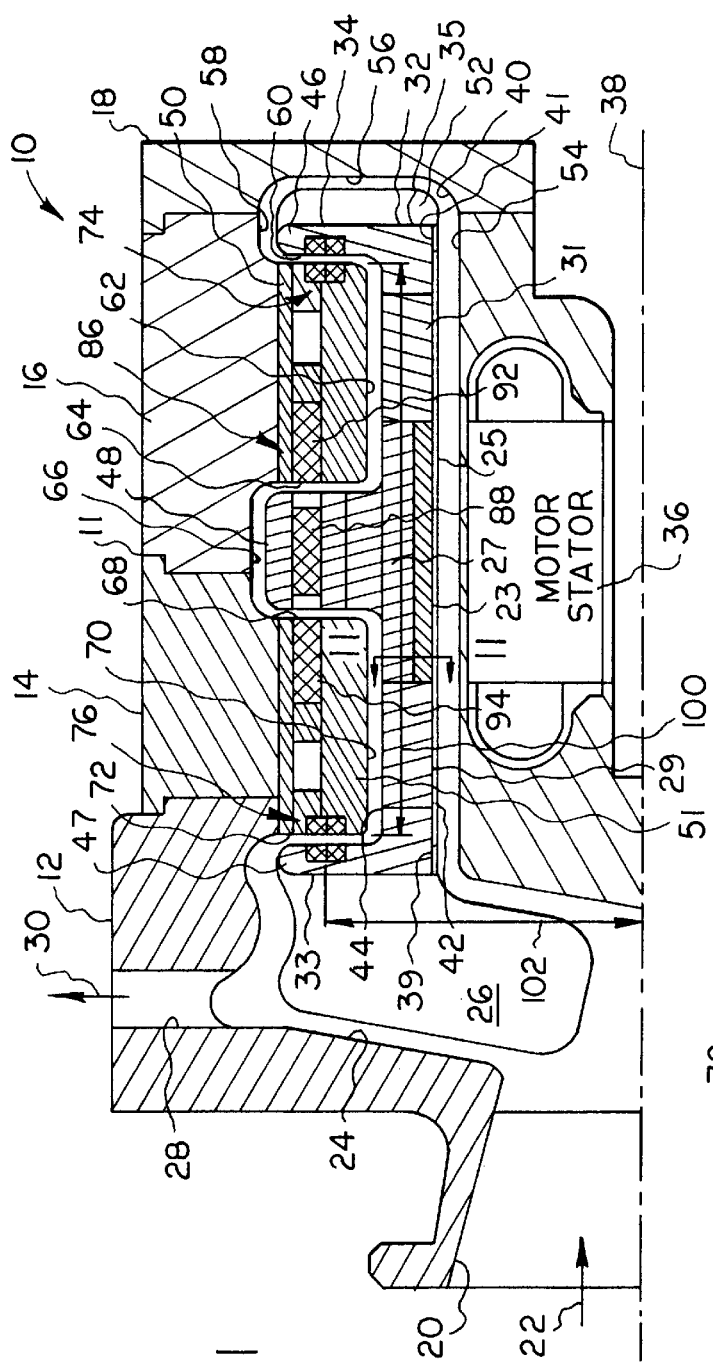
FIG. 1 is a half sectional view taken in an axial plane of a pump which embodies the present invention.
Figure 12:
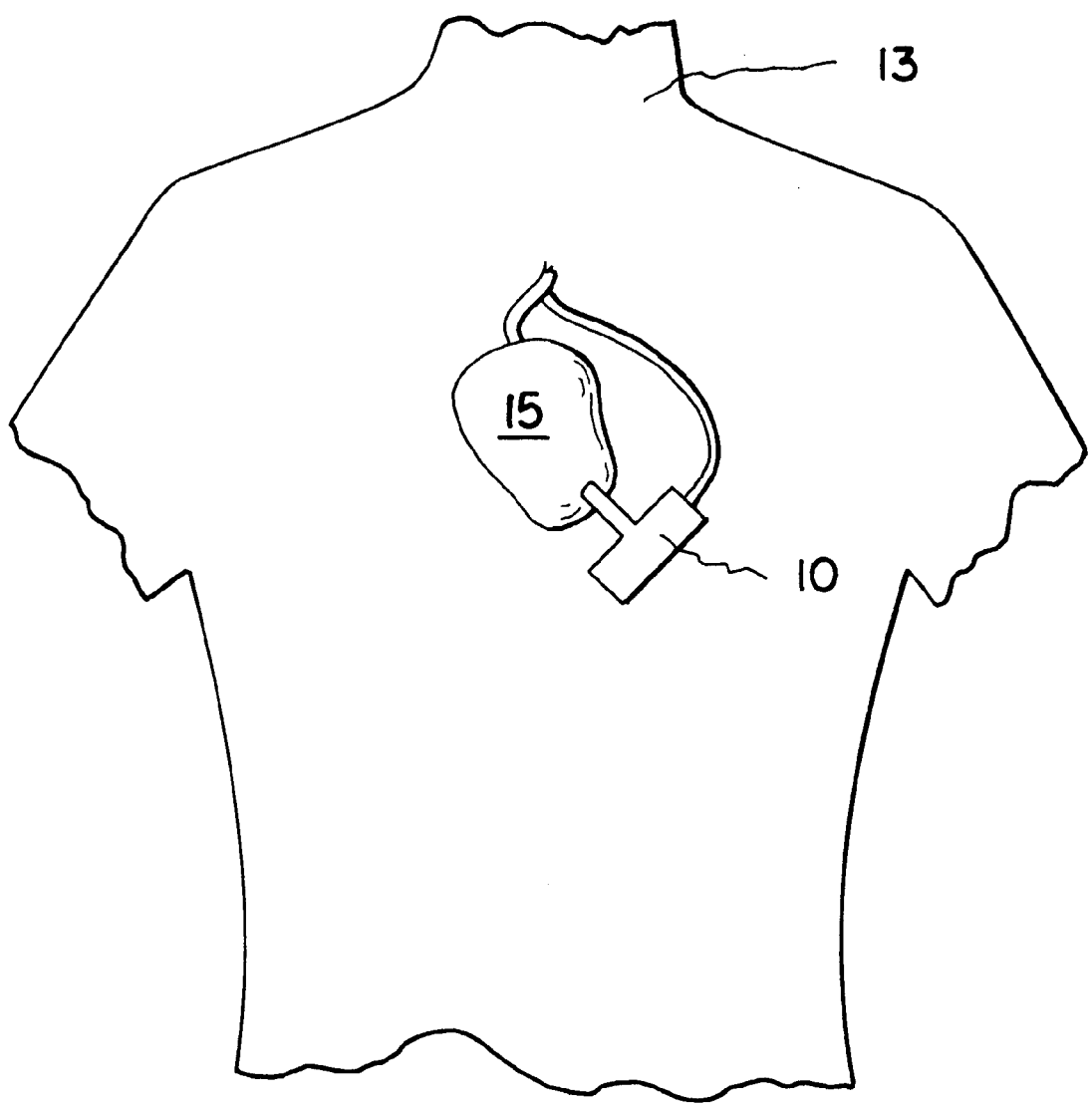
FIG. 12 is a schematic view of the pump of FIG. 1 inserted in a human body.

Referring to FIG. 1, there is shown generally at 10 a pump which may be implanted into the human body illustrated at 13 in FIG. 12, to assist the heart 15 in pumping blood through the circulatory system. However, it should be understood that a pump in accordance with the present invention may have other uses. The pump 10 has a housing 11 including housing sections 12, 14, 16, and 18. All materials with which the blood or other material comes into contact are composed of a material which is biocompatible with the blood/fluid or are suitably coated with a suitable biocompatible material such as, for example, titanium. Section 18 defines a closed end of the pump. Section 12 defines the other end of the pump and has a centrally disposed opening, illustrated at 20, defining an inlet for receiving blood or other fluid into the pump, as illustrated at 22. The blood flows into an impeller chamber, illustrated at 24, in which is contained an impeller 26. The blood is discharged, as illustrated at 30, from the impeller chamber 24 and from the pump via an outlet, illustrated at 28, formed in the radially outer wall of section 12, as is conventionally known in the art.

The impeller 26 is rotatably driven for forcing the blood through the pump by a brushless motor 32 which is suitably sealingly received within the housing 11. The motor 32 is of an inside-out type, i.e., it includes a doughnut-shaped (in cross section) rotor 34 within which is disposed a generally cylindrical stator 36. In other words, as shown in FIG. 1, the rotor 34 has a bore, illustrated at 42, extending axially therethrough, and the stator 36 is received within the bore 42 of rotor 34. The rotor 34 is magnetically suspended, as discussed hereinafter, between the centrally disposed stator 36 and the housing 11 for rotation about its rotational axis, illustrated at 38.

The inner surface or bore 42 of the rotor 34 is of generally uniform diameter over its length. The rotor 34 is shown to be composed of 5 sections stacked axially about a thin sleeve 25, e.g., a central section 27, two outer sections 33 and 35, and two sections 29 and 31 stacked between the central section and the outer sections 33 and 35 respectively. The outer sections 33 and 35 are threadedly connected to the sleeve 25 by means of threaded connections 39 and 41 respectively. The impeller 26 is suitably attached to section 33 for rotation thereof. During pumping, blood flows in the passage, illustrated at 40, between the rotor 34 and the stator 36 and between the rotor 34 and the housing 11.

Figure 11:
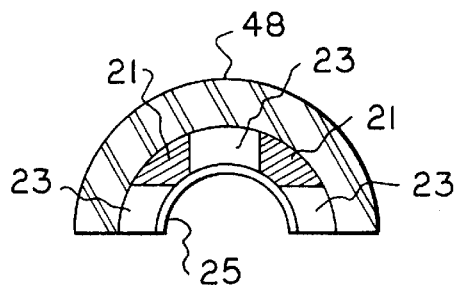
FIG. 11 is a reduced size half sectional view taken along lines 11—11 of FIG. 1.

The motor 32 is of a type wherein the rotor 34 utilizes NdFeB permanent magnets and is preferably an ironless or a surface wound type with minimum radial pull or negative radial stiffness. As seen in FIG. 11, the rotor 34 has 4 permanent magnets 23 spaced circumferentially on the central section 27 and held in position by suitable potting material 21. The central section 27, as well as the other sections 29, 31, 33, and 35, is composed of ferromagnetic material so as to confine the flux of magnets 23 to act radially inwardly. By "ironless" is meant that the stator does not contain ferromagnetic cores or the rotor does not contain ferromagnetic material so that the negative spring effect (side pull) can be reduced whereby the radial bearings (described hereinafter) may be less stiff and smaller. However, in accordance with the present invention, the motor 34 may be of any other suitable type.

The rotor 34 has an outer surface 44 which is of generally uniform diameter over a substantial portion of its length but which has a plurality of radial projections extending circumferentially therearound, as hereinafter discussed. As used herein and in the claims, unless otherwise noted, the terms "radial" or "radially" are meant to refer to direction toward or away from the rotational axis, illustrated at 38, of the rotor 34, and the terms "axial" or "axially" are meant to refer to direction parallel to the rotational axis 38 of the rotor 34. Two of these projections, illustrated at 46 and 47, are portions respectively of the outer sections 35 and 33 respectively and are therefore are located at the axially outer ends respectively of the rotor 34. A third of these projections, illustrated at 48, is a portion of the central section 27 and is thus intermediate the projections 46 and 47. Rings 50 and 51 of ferromagnetic material such as, for example, silicon steel or iron are received between the outer projections 46 and 47 respectively and the central projection 48 and are suitably attached to the housing 11. A secondary or auxiliary impeller 52 is suitably attached to the outer section 35 for enhancing/ assisting/forcing blood flow through the radial gaps (described hereinafter) of passage 40 in order to prevent stagnation of the blood. The passage 40 comprises a series or axially and radially extending segments defining fluid gaps. Thus, the passage 40 comprises an axially extending gap 54 between the rotor 34 and the stator 36, a gap 56 extending radially outwardly from gap 54 and lying between the outer projection 46 and housing section 18, a gap 58 extending axially inwardly from gap 56 and lying between the outer projection 46 and sections 16 and 18 of the housing 11, a gap 60 extending radially inwardly from gap 58 and lying between the outer projection 46 and housing member 50, a gap 62 extending axially inwardly from gap 60 and lying between surface 44 and housing member 50, a gap 64 extending radially outwardly from gap 62 and lying between the central projection 48 and housing member 50, a gap 66 extending axially from gap 64 and lying between the central projection 48 and sections 14 and 16 of the housing 11, a gap 68 extending radially inwardly from gap 66 and lying between the central projection 48 and housing member 51, a gap 70 extending axially outwardly from gap 68 and lying between surface 44 and housing member 51, and a gap 72 extending radially outwardly from gap 70 and lying between housing member 51 and outer projection 47. Unless otherwise specified, the term "housing" is defined herein and in the claims to include a stator.

Figure 2:
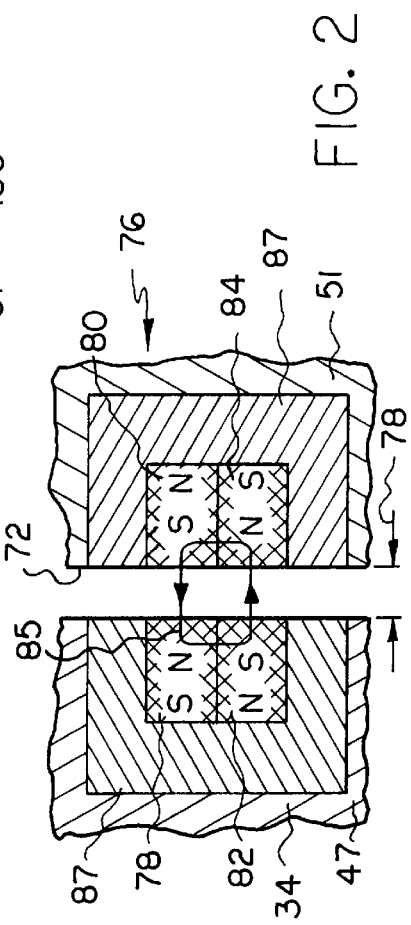
FIG. 2 is a partial detail view, similar to that of FIG. 1, thereof illustrating a radial bearing therefor.

In order to suspend the rotor 34 radially, a pair of radial or journal bearings, illustrated generally at 74 and 76, are disposed along radially extending fluid gaps 60 and 72 respectively, as discussed hereinafter. The radial bearing 76 will be described hereinafter. Since the radial bearing 74 is identical thereto, it will not be described in detail. Referring to FIG. 2, the radial bearing 76 is shown to include a first pair of axially polarized passive permanent magnet rings 78 and 80 suitably embedded in the rotor 34 and housing member 51 respectively and disposed to be in magnetically interactive facing relationship across the radially extending fluid gap 72. By "passive" is meant not connected to an electrical source for control of the magnetic flux, as contrasted with "active" which is so connected. The magnet rings 78 and 80 are each preferably rectangular in cross section and made of NdFeB or other suitable permanent magnetic material such as rare earth permanent magnetic (rare earth and cobalt) material. The magnets 78 and 80 are disposed so that the north pole, designated N, of one magnet 78 faces the south pole, designated S, of the facing magnet 80, as shown in FIG. 2. The radial bearing 76 is shown to also include a second pair of axially polarized passive permanent magnet rings 82 and 84 which are similar to magnet rings 78 and 80 and which are likewise suitably embedded in the rotor 34 and housing member 51 respectively and disposed to be in magnetically interactive facing relationship across the radially extending fluid gap 72. The magnets 82 and 84 are disposed so that the north pole, designated N, of one magnet 84 faces the south pole, designated S, of the facing magnet 82, as shown in FIG. 2. The magnetic strengths of the magnet rings 78, 80, 82, and 84 are preferably identical. Magnet 82 is disposed to be concentric with, radially inwardly of, and adjacent magnet 78. Likewise, magnet 84 is disposed to be concentric with, radially inwardly of, and adjacent magnet 80.

The polarization arrangement of the magnets 78, 80, 82, and 84 is selected to maximize the flux density at the fluid gap 72 and thus the restoring (radially shearing) force as a bearing thereby to maximize radial stiffness. Accordingly, whereas the north pole N of magnet 78 faces the gap 72, the opposite or south pole S of adjacent magnet 82 faces the gap 72. Likewise, whereas the south pole S of magnet 80 faces the gap 72, the opposite or north pole N of adjacent magnet 84 faces the gap 72. As a result, a generally circular flux arrangement, illustrated at 85, is achieved for maximizing radial stiffness. The first pair of magnets 78 and 80 are in an attractive magnetic relationship to keep them from moving radially apart, and the second pair of magnets 82 and 84 are also in an attractive magnetic relationship to keep them from moving radially apart. Thus, if there is a tendency of the rotor 34 to move either radially inwardly or radially outwardly, the magnetic attractive force between the first pair of magnets 78 and 80 and the magnetic attractive force between the second pair of magnets 82 and 84 will act to prevent this from occurring so that the radial position of the rotor 34 is maintained in the position shown in FIGS. 1 and 2 with magnets 78 and 80 facing each other and magnets 82 and 84 facing each other. Furthermore, the magnetic repulsive force between the south poles S of magnets 82 and 80 will act to prevent the rotor 34 from moving radially outwardly (which would bring the south poles of magnets 82 and 80 closer to each other), and the magnetic repulsive force between the north poles N of magnets 78 and 84 will act to prevent the rotor 34 from moving radially inwardly (which would bring the north poles of magnets 78 and 84 closer to each other). Thus, the pairs of magnets 76 are provided to stabilize the rotor 34 in a desired position radially and thereby act as a radial or journal bearing. While two pairs of facing magnet rings are shown to comprise radial bearing 76, it should be understood that, in accordance with the present invention, radial bearing 76 may comprise a greater number of such pairs of facing magnet rings. While it is preferred that the magnet rings in each adjacent pair be closely adjacent each other so as to touch each other as shown to maximize the restoring force between magnets in adjacent pairs on opposite sides of the gap 72, it should be understood that, in accordance with the present invention, there may be some spacing between some or all of the adjacent pairs of magnets.

It is considered desirable that the axial stiffness of the radial bearing 76 be minimized so as to minimize the power needed for the axial or thrust bearing 86 to overcome such axial stiffness. In order to minimize axial stiffness of bearing 76, the magnets 78, 80, 82, and 84 are preferably suitably encased in a suitable non-magnetic material, illustrated at 87 only in FIG. 2, such as, for example, aluminum whereby the ratio of axial to radial stiffness of bearing 76 may be reduced, for example, from 5 or more to about 2. In this regard, see page 1170 of the aforesaid Yonnet reference.

Figure 3:
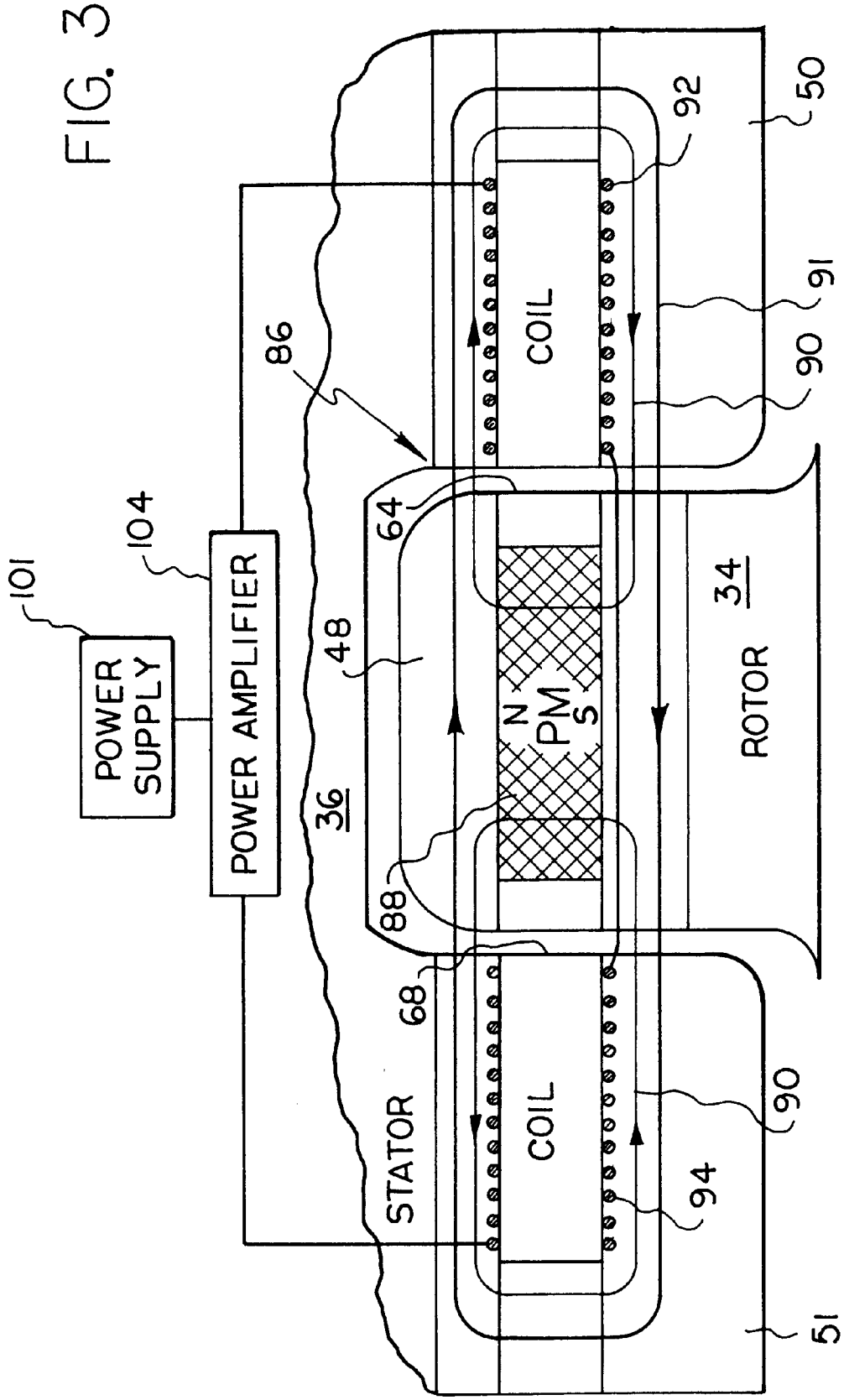
FIG. 3 is an enlarged partial detail view, similar to that of FIG. 1, thereof illustrating the thrust bearing therefor.

In order to maintain a desired clearance for blood flow (without damage to individual blood cells) within the radially extending gaps 56, 60, 64, 68, and 72 as well as within the remainder of passage 42, an active thrust magnetic bearing, illustrated generally at 86, is disposed across radially extending gaps 64 and 68 to control the axial position of the rotor 34. The clearance required to be maintained by the thrust bearing 86 so as not to damage blood cells is related to the local flow velocity and pressure and may be as little as 0.020 inch or perhaps less. Referring to FIG. 3, the thrust bearing 86 comprises a radially polarized permanent magnetic ring 88 suitably embedded in the central radial projection 48 adjacent the radially extending fluid gaps 64 and 68 respectively to provide bias flux, illustrated at 90, so that power consumption by the active thrust bearing 86 may be minimized. The thrust bearing 86 also comprises a pair of electrically powered magnetizing coils, illustrated at 92 and 94, wound on cores and suitably embedded in the housing members 50 and 51 respectively to be adjacent the radially extending gaps 64 and 68 respectively in facing relationship with the magnet ring 88 for magnetic interaction therebetween respectively for control flux, illustrated at 91. As illustrated in FIG. 3, the magnetizing coils 92 and 94 are connected in series and driven by a linear or other suitable power amplifier 104, which is suitably connected to a suitable power supply 101 for supply of electrical power thereto. Depending on the direction of current flow to the coils 92 and 94, the direction of magnetic flux 91 will be in one direction to be additive to the permanent magnet flux 90 across fluid gap 64 or in the other direction to be additive to the permanent magnet flux 90 across fluid gap 68. As the directions of coil flux 90 and 91 are illustrated in FIG. 3 by arrows, the coil flux 91 is additive to the permanent magnet flux 90 across fluid gap 64 and subtractive to the permanent magnet flux 90 across fluid gap 68. This will urge the magnet 88 and thus the rotor 34 toward the right, as viewed in FIG. 3, to widen the gap 68 while narrowing the gap 64. By reversing the current to coils 92 and 94, the coil flux 91 will be additive to the permanent magnet flux 90 across fluid gap 68 thereby urging the magnet 88 toward the left to widen the gap 64 while narrowing the gap 68. Thus, by controlling the direction as well as magnitude of electrical current to magnetizing coils 92 and 94, the position axially of the rotor 34 may be controlled to maintain the desired spacing across the radially extending gaps 56, 60, 64, 68, and 72. If desired, the coils 92 and 94 may be separately powered or powered in parallel, although this would undesirably require another power amplifier.

Magnet rings having radial polarity are difficult to manufacture. Therefore, for manufacturing ease, the permanent magnet 88 may be comprised of a plurality of, for example, 8 ring segments arranged circumferentially to form a ring.

Figure 5:
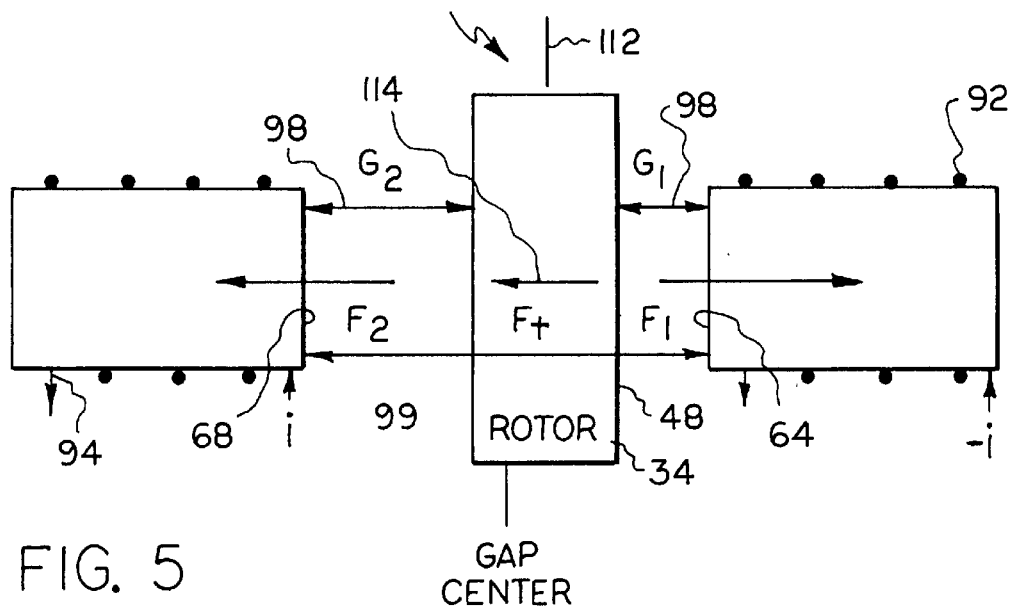
FIG. 5 is a schematic of the thrust bearing illustrating a static force equilibrium position of the rotor for the pump motor.

It is considered desirable that the width, illustrated at 78 in FIG. 2, of each of the radial bearing gaps 60 and 72 as well as the total of the widths, illustrated at 98 in FIG. 5, of the thrust bearing gaps 64 and 68 be minimized to maximize bearing stiffness, i.e., the ability of a bearing to resist momentary excursions. In order that momentary radial excursions of the rotor 34 not unduly affect radial gap width or that momentary axial excursions of the rotor 34 not unduly affect axial gap width as well as to minimize the widths 78 and 98 of the radial and thrust bearing gaps respectively, each of the radially extending gaps 56, 60, 64, 68, and 72 desirably extends in a direction substantially normal to the rotational axis 38, and each of the axially extending gaps 54, 58, 62, 66, and 70 desirably extends in a direction substantially parallel to the rotational axis 38. Thus, in order to maintain sufficient clearance so as not to damage blood cells while minimizing the clearance so as to maximize bearing stiffness, the respective gap widths 78 and 98 for bearing gaps 60, 64, 68, and 72 may, for example, be kept to about 0.02 inch, but the gap width in the remainder of passage 42 may be increased to further provide added assurance that blood cells will not be damaged. For pumping fluids other than blood where damage to blood cells need not be considered, the gap widths 78 and 98 may be decreased below 0.02 inch to provide greater bearing stiffness.

The radial stiffness $K_r$ can be estimated, as discussed in the aforesaid J. Yonnet reference, using the following equation for a stator permanent magnet ring with a rotor ring:

$$K_r = CPB^2A^2/D^4 \text{ N/m}$$

where B is the permanent magnet residue flux density in tesla, A is the permanent magnet ring cross-sectional area in square meters, D is the average distance between permanent magnet rings in meters, P is the average perimeter of the permanent magnet rings in meters, and C is the constant $$6/4\pi(4\pi10^{-7})$$

The above formula may be applied to all the combinations of the stator and rotor rings for the radial bearings 74 and 76 and the results summed to calculate the total radial stiffness. For example, for the pump 10, there would be four pairing combinations for the radial bearing 74 and four pairing combinations for the radial bearing 76. If the total radial stiffness of either of the bearings 74 and 76 is greater than the motor radial negative stiffness, the rotor would be statically stable in the radial direction.

There is an angular negative stiffness associated with the axial attractive forces of the magnetic rings, which stiffness $K_\theta$ is approximately $$F_a R_m^2/g$$

where $F_a$ is the total axial attractive force at the radial fluid gaps, $R_m$ is the average radius of the distributed force (defined hereinafter), and g is the fluid gap width. The amount of restoring angular stiffness $K_\theta'$ due to the radial stiffness at the fluid gaps is $$kL^2/2$$

where k is the radial stiffness at each fluid gap and L is the bearing span (axial distance between fluid gaps). The cause of static instability, i.e., $K_\theta$ greater than $K_\theta'$, indicates generally that the average radius is too large or the bearing span is too small.

In order to stabilize the rotor 34 statically, in accordance with the present invention, the bearing span, illustrated at 100, is provided to be at least about 2½ times, preferably 3 or more times, greater than the average radius, illustrated at 102, of the distributed force, which is defined hereafter. The bearing span 100 may be defined as the distance between the fluid gaps for the axially outer radial bearings. The average radius of the distributed force for a permanent magnet bearing having a plurality of pairs of permanent magnet rings closely packed together to have an inner radius and an outer radius may be defined as the square root of half of the sum of the squares of the inner radius and the outer radius, and, for two pairs of permanent magnets as shown in FIG. 1, may be approximated as illustrated in FIG. 1.

Figure 4:
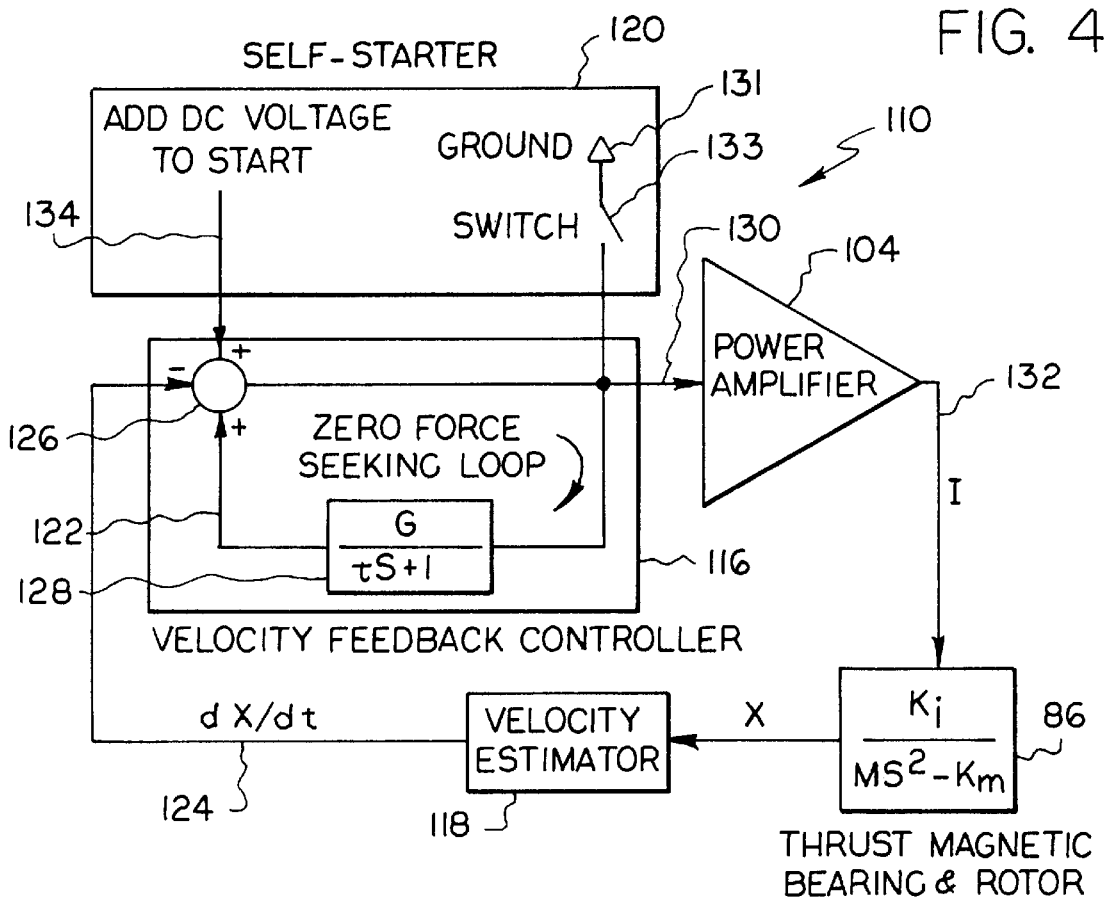
FIG. 4 is a schematic of a feedback control system for a thrust bearing for the pump.

In order to provide a feedback control system for the thrust bearing 86 which is inexpensive, robust, and reliable, in accordance with a preferred embodiment of the present invention, the currrent to the magnetizing coils 92 and 94 is controlled by velocity feedback control circuitry, illustrated at 110 in FIG. 4. My aforesaid U.S. Pat. No. 5,666,014 discloses velocity feedback control circuitry for radial bearings. As hereinafter described, this circuitry of my aforesaid '014 patent may be adapted for the thrust bearing of the present invention, i.e., for the magnetizing flux in gaps 64 and 68.

Referring to FIG. 5, velocity feedback control is based on the existence of a static force equilibrium or balance position, illustrated at 112, in the bearing clearance, illustrated at 99. This position 112 serves as an axial displacement control reference. The velocity feedback circuitry 110 is provided to regulate the supply of current from amplifier 104 in order to create modulating magnetic forces to keep the rotor 34 at this position 112. FIG. 5 shows that the balance or equilibrium position is slightly off to the right, as viewed in FIG. 5, due to a static load, illustrated at 114, applied on the rotor 34, assuming that the two electromagnets 92 and 94 are equally strong. When the static load changes, the rotor 34 will automatically settle at a new balance position. The new balance position will, however, not be a stable one without the feedback control provided by circuitry 110. This has been classically termed "unstable equilibrium." Its like balancing a vertical stick from one's hand; the bottom of the stick must be moved around to keep the stick standing up.

It should be emphasized that the active thrust bearing static stiffness is very different from, usually much higher than, its dynamic stiffness. In general, an active magnetic bearing stiffness is a function of excitation frequency. For velocity control of the bearings of motor 32, the static stiffness is equal to the sum of negative stiffnesses due to the two passive radial bearings 74 and 76 and those due to permanent magnet bias flux in the thrust bearing gaps 64 and 68.

Referring again to FIG. 4, the feedback control circuitry 110 comprises a velocity feedback controller 116, a velocity estimator 118, and a self-starter 120. See H. M. Chen (the inventor of the present invention), "Design and Analysis of a Sensorless Magnetic Damper," presented at ASME Turbo Expo, Jun. 5–8, 1995, Houston, Tex., 95GT180, as well as the aforesaid Chen patent. The velocity feedback controller contains a positive feedback loop 122 which may be called a zero force seeking loop. When the average rotor position is not at a static balance point, the rotor 34 will be accelerated toward one side, and the corresponding velocity signal outputted on line 124 from the velocity estimator 118 will show this one-sided effect, and this signal will be inputted to summer 126. The zero force seeking loop has a low pass filter, illustrated at 128, for detecting this acceleration, and, with its positive feedback, magnifying this effect. It then provides signals through lines 130, which are amplified by power amplifiers 104, and amplified corrective signals are then sent via lines 132 to the magnetizing coils 92 and 94 for the magnetizing flux to be increased in one and to be decreased in the other.

In order to obtain rotor velocity for input to velocity estimator 118, the back EMF across a magnetizing coil 92 or 94 and the signal of the current flowing through the coil may be tapped, and the rotor vibration velocity recreated digitally or by analog means. Since this sensorless method is sensitive to coil temperature which affects the copper wire electrical resistance, suitable search coils may be used to pick up the EMF and eliminate the current variation part of the signal. Alternatively, a velocity probe using a permanent magnet moving inside a coil may be used. Other suitable methods for obtaining rotor velocity may be used.

Figure 6:
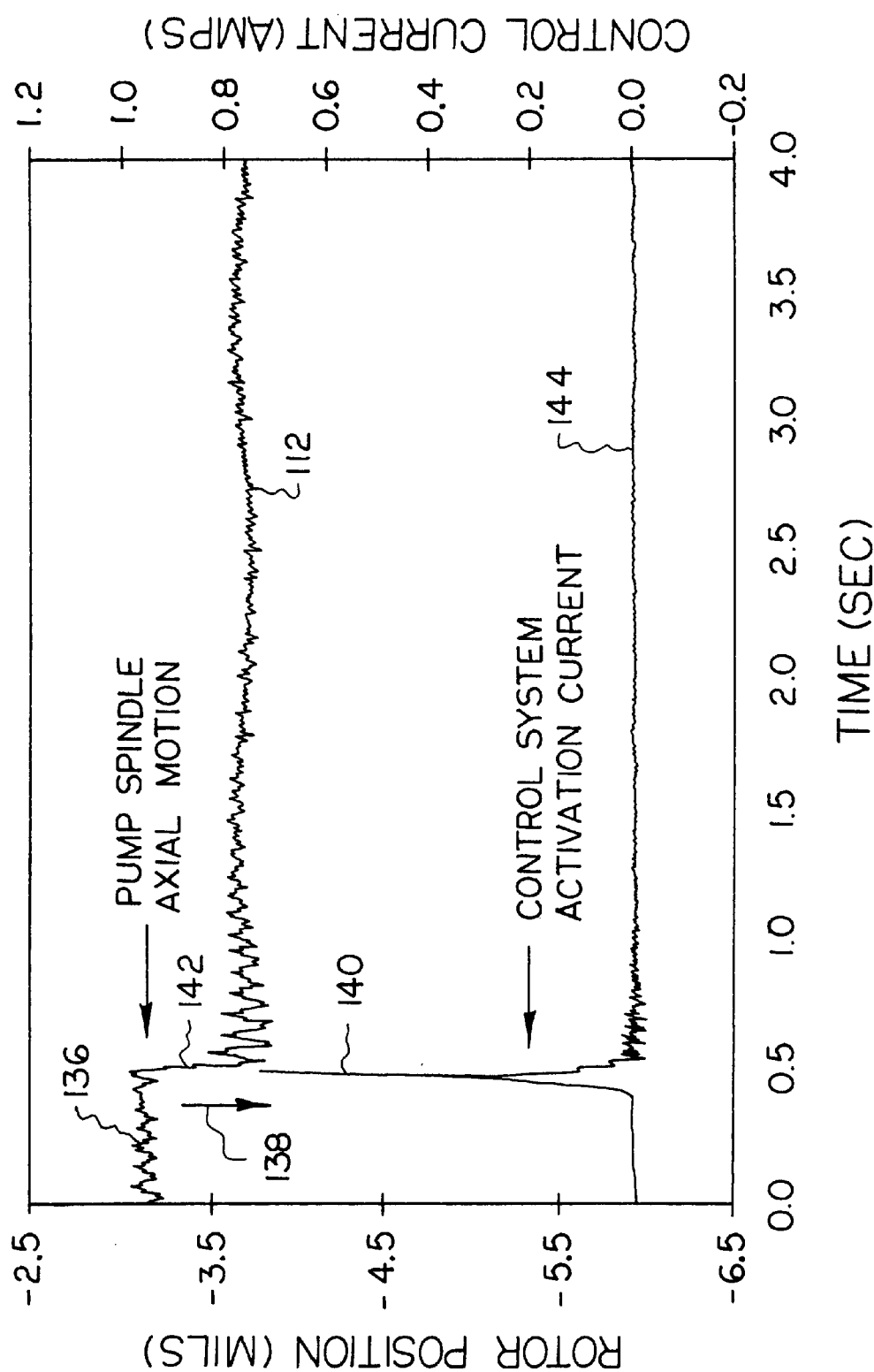
FIG. 6 is a graph illustrating usage of current and rotor position during levitation of the rotor, but not including usage of current for correcting for disturbances during rotation thereof.

Since the control circuitry 110 is activated by velocity, the rotor 34 at rest, as illustrated at the position illustrated at 136 in FIG. 6, needs a "kick" to get the magnetic levitation started. Before "kicking" the rotor 34, it is necessary to know which side of the magnets the rotor is resting or leaning on. The "kick" should be in the direction, as illustrated at 138 in FIG. 6, to "free" the rotor 34. When the rotor 34 is at rest, the zero force seeking loop output is to ground, illustrated at 131, and the ground switch 133 is closed. To initiate a "start," a small DC voltage, with the correct sign for the direction in which the "kick" is to be made, is applied through line 134 to summer 126, and the grounding switch 133 is simultaneously opened. The zero force seeking loop 122 will then integrate this DC signal and demand a current, which will then be amplified by the amplifier 104, and the amplified current, illustrated at 140 in FIG. 6, applied via the appropriate line 132 to the appropriate magnetizing coil 92 or 94 to "shoot" the rotor 34 into the "air," as illustrated at 142 in FIG. 6. The velocity feedback controller 116 would then "grab" the rotor 34 in the "air," so to speak. After the levitation, the DC voltage is then removed from line 134, and the "start" process is complete.

Since the bias flux is created with the permanent magnet 88, the thrust bearing 86 consumes essentially no power, as illustrated at 144 by the near zero control current, for maintaining the rotor substantially at the balance or equilibrium position 112. As in other conventional bearing-rotor systems, some amount of dynamic current may still be needed to counteract disturbances such as those due to unbalanced forces. For example, the power consumption may be less than about ½ watt compared to about 5 watts or more for conventional control systems.

Alternatively, conventional PID (proportional-integral-derivative) displacement feedback control circuitry or other suitable feedback circuitry may be provided for controlling the power to magnetizing coils 92 and 94 to maintain the desired rotor axial position.

For example, a pump according to the embodiment of FIGS. 1 to 6 may be provided to desirably achieve a size smaller than 4 inches in diameter and 5 inches in length so that it may be smaller than or compete size-wise with conventional pumps with magnetic bearings.

It should be understood that, alternatively, a pump may be constructed in accordance with the present invention wherein one or more radial gaps corresponding to radial gaps 60, 64, 68, and 72 may be between the rotor 34 and the stator 36, such as in the embodiments of the present invention discussed hereinafter.

As seen in FIG. 1, it is difficult to keep the thin plates 46 and 47, to which the magnet rings 78, 80, 82, and 84 are glued or otherwise suitably attached, sufficiently rigid to alleviate wavyness in the axial direction, which can cause rotor vibration during rotation. Increasing the thickness of backing plates 46 and 47 to achieve the desired rigidity adds a weight penalty. The use of the large diameter radial bearing rings may also result in a larger than desired pump, especially when it is considered that the bearing span must also be increased to achieve the desired ratio of bearing span to the average radius of distributed force, as hereinbefore discussed. In order to decrease the radial bearing diameter of a pump so as to reduce the pump overall size as well as to eliminate the "wavyness" problem, in accordance with an alternative embodiment of the present invention, a pump, illustrated generally at 200 in FIG. 7, is provided wherein a pair of radial bearings, illustrated at 202 and one of which is illustrated in FIG. 8, each comprises a plurality of axially stacked smaller diameter permanent magnet rings 204 on the stator 208 of motor 220 and a corresponding plurality of axially stacked permanent magnet rings 206 on the rotor 218 of motor 220 which face across an axially extending fluid gap, illustrated at 210, for interaction magnetically with each other, the gap 210 extending in a direction which is substantially parallel to the rotational axis, illustrated at 212 in FIG. 8, of the pump 200.

Figure 7:
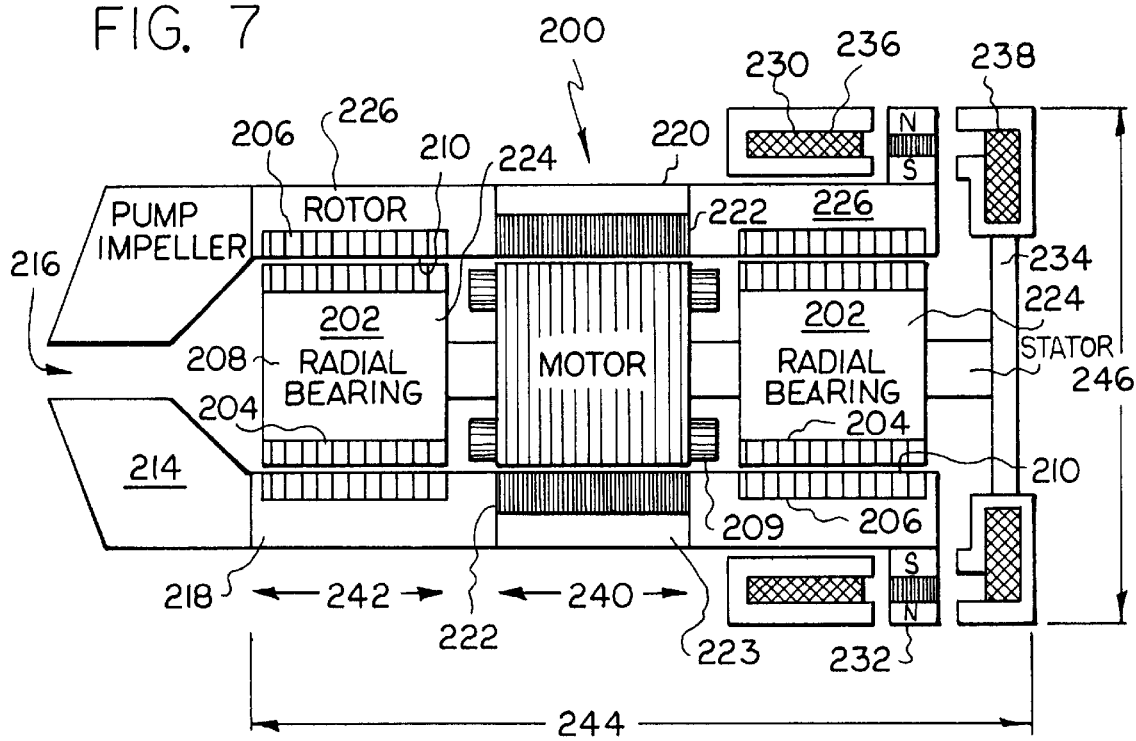
FIG. 7 is a schematic view taken in an axial plane of a pump in accordance with an alternative embodiment of the present invention.
Figure 8:
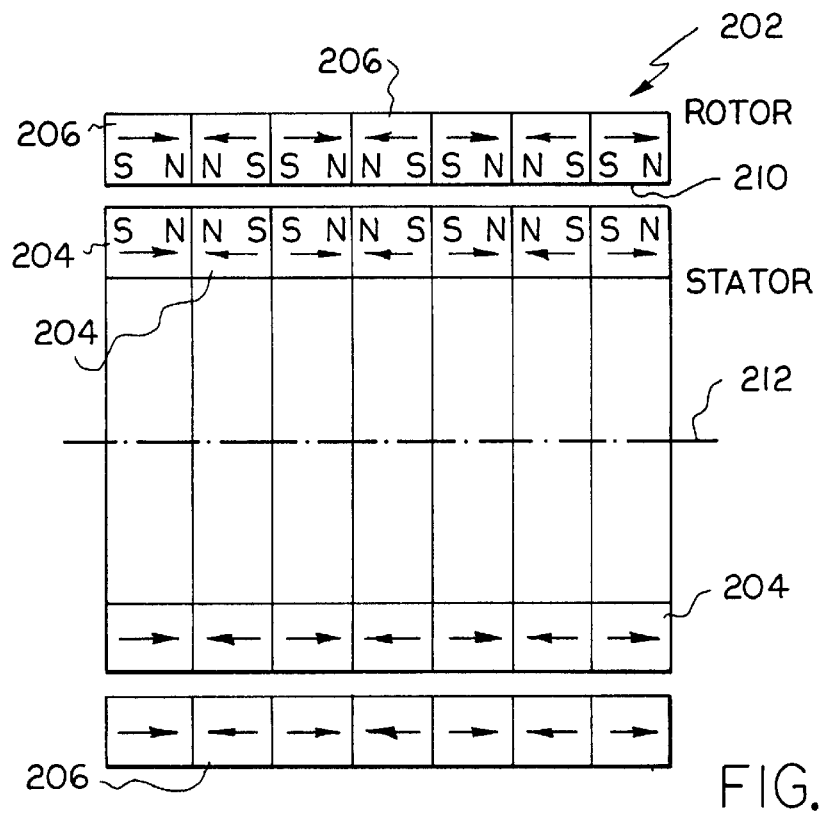
FIG. 8 is a schematic illustration taken in an axial plane of one of the journal or radial bearings for the pump of FIG. 7.

As seen in FIG. 7, the stator 208 is received within the rotor 218, and the assembly is suitably sealingly enclosed within a housing (not shown) in accordance with principles commonly known to those of ordinary skill in the art to which this invention pertains. A pump impeller 214 is suitably attached to one end of the rotor 218 for moving or forcing fluid from an inlet, illustrated at 216, through an outlet (not shown) as conventionally known in the art.

The motor 220 conventionally includes suitable electrically supplied electromagnetic coils, illustrated at 209, on the stator 208 with which permanent magnets, illustrated at 222, disposed on the rotor in circumferentially surrounding relation to the coils 209, magnetically interact, as is conventionally known in the art, to effect rotation of the rotor 218 and thereby motive force of the impeller 214 for pumping of fluid. The magnets 222 are desirably surrounded radially by an outer ring 223 of ferromagnetic material to confine the flux radially inwardly. The magnets 222 and outer ring 223 are similar to and disposed similarly as illustrated in FIG. 11 for magnets 23 and the outer ring 48 for the motor for pump 10.

In accordance with the present invention, the stator 208 has a cylindrical axial extension, illustrated at 224, extending from each of the axial sides of the portion thereof containing the motor magnets 222. The radial bearing magnets 204 are suitably mounted on these axial extensions 224 respectively in the radially outer surfaces respectively thereof. The corresponding radial bearing magnets 206 are mounted in the radially inner surfaces of axial extensions, illustrated at 226, extending from each of the axial sides of the portion of the rotor 218 containing the motor magnets 222, so as to be axially aligned with magnets 222 across the fluid gaps 210 respectively for magnet interaction therebetween.

Referring to FIG. 8, each of the magnet rings 204 and 206 is axially polarized and are oriented relative to each other across the gap 210 so as to provide a repulsive relationship between each magnet ring 204 and the corresponding facing magnet ring 206 across the gap 210. Thus, as seen in FIG. 8, for each pair of facing magnet rings 204 and 206, a south pole on one faces a south pole on the other and a north pole on one faces a north pole on the other so that the magnet rings repulse each other, and this repulsive force is provided to maintain the axial gap 210 during rotation of the rotor 218. Magnet rings 204 are oriented so that a south pole on one magnet ring 204 faces a south pole on an adjacent magnet ring 204 and a north pole on one magnet ring 204 faces a north pole on an adjacent magnet ring 204. Likewise, Magnet rings 206 are oriented so that a south pole on one magnet ring 206 faces a south pole on an adjacent magnet ring 206 and a north pole on one magnet ring 206 faces a north pole on an adjacent magnet ring 206.

In order to mount the magnet rings 204, the axial extension 202 may be provided with a reduced diameter portion for receiving the rings and a shoulder at its inner end for the inner ring to bear against, and a nut may be applied to the other end to compress the magnet rings together onto the extension 202. Similarly, the rotor 218 may have shoulders for the inner magnet rings 204 to bear against, and a plug may be applied to the outer ends to compress the magnet rings respectively together.

Referring again to FIG. 7, the pump 200 also has a thrust bearing, illustrated at 230, which includes a radially polarized permanent magnet ring 232 (which, for ease of construction, may comprise a plurality of circumferential segments, similarly as previously discussed for thrust bearing magnet ring 88) suitably mounted to the radially outer surface of rotor 218 at the end thereof which is opposite the impeller end. On opposite axial sides of the magnet ring 232 are suitably mounted to the housing and a radial extension 234 of the stator 208 respectively are a pair of electromagnetic coils 236 and 238 respectively for magnetic interaction with the magnet ring 232 to control the position axially of the rotor 218.

The motor section (containing the motor magnets and motor coils), may have a width, illustrated at 240, of, for example, about 0.5 inch, and each of the extensions 224 may have a width, illustrated at 242, of, for example, about 0.5 inch so that the overall pump length, illustrated at 244, exclusive of the impeller and housing, may, for example, be about 2.4 inches. By providing the smaller diameter radial bearing magnet rings 204 and 206, the overall pump diameter, illustrated at 246, exclusive of the housing, may be desirably reduced to, for example, about 1.5 inches. Thus, the bearing assembly of FIG. 7 is provided to minimize overall pump size while providing a bearing span which is at least 2½ times an average radius of the distributed force, in accordance with principles previously discussed with respect to the embodiment of FIGS. 1 to 6.

Figure 9:
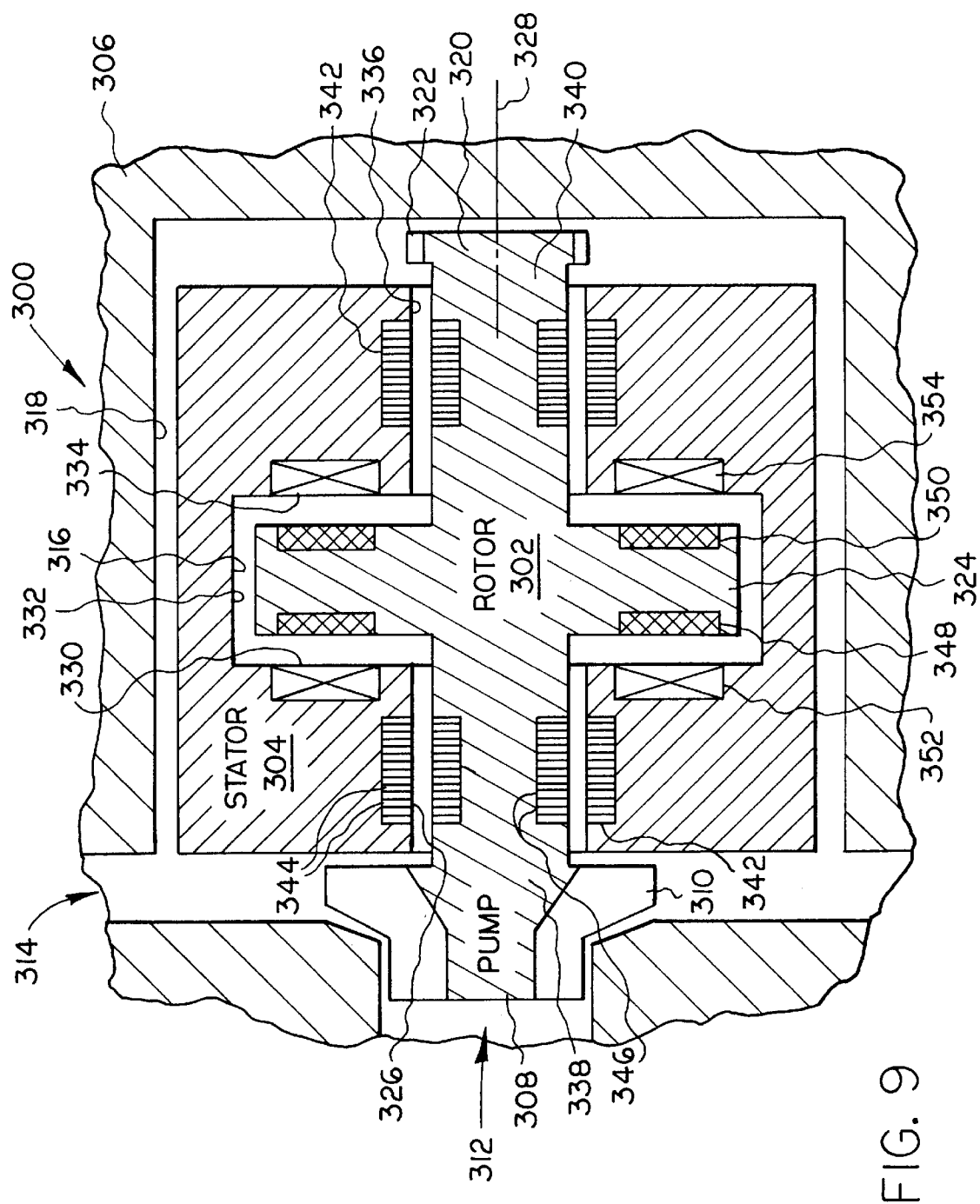
FIG. 9 is a schematic view taken in an axial plane of a pump in accordance with another alternative embodiment of the present invention.

While the embodiments of the present invention which have been described show a stator received within a rotor, an embodiment of the present invention is envisioned wherein the rotor is received within the stator. Such an embodiment of a pump is illustrated generally at 300 in FIG. 9. Pump 300 includes a rotor 302 rotatably received within a stator 304, and the assembly is suitably sealingly received within a housing 306. One end of the rotor 302 is suitably attached to an impeller 308, which includes blades 310, for forcing a fluid from an inlet, illustrated at 312, through an outlet, illustrated at 314. The fluid also flows through passages 316 and 318 between the rotor 302 and stator 304 and between the stator 304 and housing 306 respectively. The stator 304 is non-rotatably anchored to the housing 306 by suitable means (not shown). An auxiliary or secondary impeller 320, having blades 322, is suitably attached to the other end of the rotor 302 to keep the fluid flowing through passages 316 and 318 to prevent stagnation thereof.

The rotor 302 is a generally cylindrical member which has an increased diameter cylindrical portion 324 intermediate its ends, which defines axial extensions 338 and 340 on opposite sides axially thereof. The stator 304 is shaped to conform to the shape of rotor 302. Thus, the fluid passage 316 between the rotor 302 and stator 304 includes a first gap 326 which extends axially (preferably in a direction substantially parallel to the pump rotational axis, illustrated at 328) inwardly from the impeller end alongside extension 338 to the intermediate rotor portion 324, a second gap 330 which extends radially (preferably in a direction substantially normal to the pump rotational axis 328) outwardly alongside the intermediate rotor portion 324 over the radial extent thereof, a third gap 332 which extends axially (preferably in a direction substantially parallel to the pump rotational axis 328) between the intermediate rotor portion 324 and the stator 304, a fourth gap 334 which extends radially (preferably in a direction substantially normal to the pump rotational axis 328) inwardly alongside the intermediate rotor portion 324 to the extension 340, and a fifth gap 336 which extends axially (preferably in a direction substantially parallel to the pump rotational axis 328) from the intermediate rotor portion 324 alongside the extension 340 to the auxiliary impeller end of the rotor 302.

A radial or journal bearing 342 is provided along each of the axial gaps 326 and 336 and includes a plurality of axially stacked and axially polarized permanent magnet rings 344 on the respective rotor extension 338 and 340 which are oriented across the respective gap from similar magnet rings 346 on the stator 304 to magnetically interact therewith respectively. The radial bearings 342 are similar to radial bearings 202.

A pair of permanent magnet rings 348 and 350 are suitably embedded in the intermediate rotor portion 324 to lie alongside the radial gaps 330 and 334 respectively. A pair of electromagnetic coil rings 352 and 354 are suitably contained in the stator 304 to also lie alongside the radial gaps 330 and 334 respectively and positioned to face the magnet rings 348 and 350 respectively for magnetic interaction therewith. Each coil ring 352 and 354 contains poles with motor windings for magnetically interacting with the respective magnet ring 348 and 350 to effect rotation of the rotor 302 in accordance with known principles and thrust bearing windings for magnetically interacting with the respective magnet ring 348 and 350 to control axial position of the rotor 302, the combination of thrust bearing windings and magnet rings 348 and 350 being similar to thrust bearing 86 except that the windings are connected to separate power amplifiers for magnetic interaction with the magnet rings 348 and 350 respectively, and the thrust bearing is operated for control of axial position of the rotor 302 similarly as described for the embodiment of FIGS. 1 to 6. Alternatively, it is envisioned that the same windings may be provided to serve as both motor and thrust bearing windings.

Figure 10:
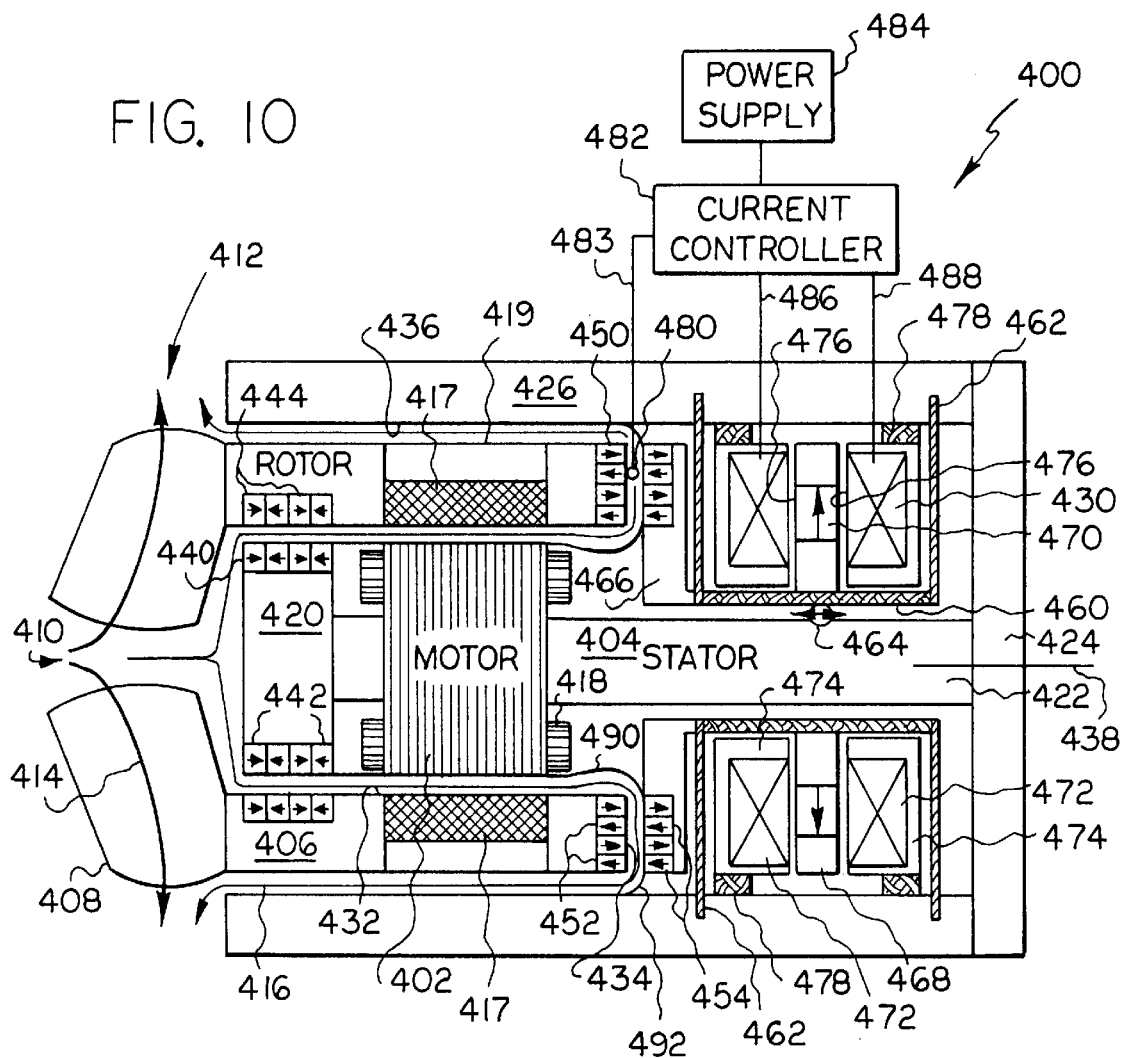
FIG. 10 is a view similar to that of FIG. 9 of a pump in accordance with yet another alternative embodiment of the present invention.

Referring to FIG. 10, there is illustrated generally at 400 a pump in accordance with another alternative embodiment of the present invention. The pump 400 comprises a motor 402 including a stator 404 received within a rotor 406 to which an impeller 408 is suitably attached to one end. The assembly is suitably sealingly contained within a housing comprising members 424 and 426. The impeller 408 receives fluid from an inlet, illustrated at 410, and forces it, as illustrated at 414, through an outlet, illustrated at 412, in accordance with principles commonly known in the art. The fluid also flows, as illustrated at 416, through passages between the rotor 406 and stator 404 and between the rotor 406 and housing member 426 then out through the outlet 412. As seen in FIG. 10, the flow path 416 around the rotor 406 is desirably less torturous.

The motor 402 is similar to motor 220, i.e., it includes circumferentially spaced permanent magnets 417 and a surrounding ring 419 of ferromagnetic material, similar to magnets 23 and ring 48 as seen in FIG. 11, on the rotor 406 and electromagnetic coils 418, similar to coils 209, on the stator 404 which magnetically interact with the magnets 417 to effect rotation of the rotor 406, as is commonly known in the art. In order that the overall size of the pump 400 may be reduced even further, the motor 402 may preferably be of the iron-less type, as previously discussed with respect to pump 10, so that the negative spring effect (side pull) can be reduced whereby the radial bearings (described hereinafter) may be less stiff and smaller.

The stator 404 has an axial extension 420 on the impeller side which is similar to an extension 202 for pump 200. To the other side, the stator 404 has a reduced diameter elongate extension 422 to the end of which is attached the enlarged diameter cylindrical housing portion 424 which extends radially beyond the rotor 406. Housing portion 426, which is sleeve-shaped, extends from the radially outer edge of portion 424 axially back toward the impeller 408 so that the rotor 406 is rotatably positioned between the housing portion 426 radially outwardly thereof and the extension 420 and stator portion containing the coils 418 radially inwardly thereof. Interposed between the axially inner end of the rotor 406 and the cylindrical portion 424 is a thrust bearing assembly 430, which will be described in greater detail hereinafter. The flow path 416 includes an axially extending fluid gap 432 between the rotor 406 and the stator extension 420 and continuing to extend axially inwardly to the thrust bearing assembly 430, a radially extending fluid gap 434 between the rotor 406 and the thrust bearing assembly 430, and an axially extending fluid gap 436 between the rotor 406 and the sleeve member 426. Preferably, each of the axial gaps 432 and 436 extends in a direction substantially parallel to the rotational axis, illustrated at 438, of the pump 400, and the radial gap 434 extends in a direction substantially normal to the axis 438, for reasons previously discussed above with reference to the embodiment of FIGS. 1 to 6.

A radial or journal bearing 440 is provided along the axial gap 432 and includes a plurality of, for example, four axially stacked and axially polarized permanent magnet rings 442 on the rotor extension 420 which are oriented across the gap from similar magnet rings 444 on the stator 406 to magnetically interact therewith. The radial bearing 440 is similar to each of radial bearings 202.

At the opposite end of the rotor 406, the rotor 406 is magnetically supported by a radial or journal bearing 450 which is provided along the radial gap 434 and includes a plurality of, for example, four radially stacked and axially polarized permanent magnet rings 452 on the rotor end which are oriented across the gap from similar magnet rings 454 to magnetically interact therewith. The radial bearing 450 is similar to radial bearing 76. In addition to acting to support the rotor 406, the bearing 450 is also part of the thrust bearing assembly 430, as hereinafter discussed.

The stator portion 422 is received within a cylinder 460 of, for example, stainless steel which is suitably connected to the stator portion 426 by a pair of discs 462 of flexible material such as, for example, thin stainless steel attached at the ends respectively of cylinder 460 and to the portion 426, allowing axial movement of cylinder 460, as illustrated at 464. A disc 466, having a central opening, illustrated at 468, in which the stator portion 422 is received, is suitably attached to the cylinder 460 so that the disc 466 moves axially as the cylinder moves. The magnet rings 454 are suitably mounted on the disc 466 so that magnet rings 454 are movable axially toward and away from magnet rings 452.

A disc 468 is suitably mounted axially centrally on the cylinder 460 and extends radially outwardly therefrom. A radially polarized permanent magnet ring 470 is suitably mounted on the disc 468, generally radially centrally thereof. A pair of electromagnetic coil assemblies 472 are mounted in ferromagnetic material in the form of rings 474 respectively to position the electromagnetic coil assemblies 472 in interactive relationship with the permanent magnet ring 470 with air gaps, illustrated at 476, separating the electromagnetic coil assemblies 472 from the permanent magnet ring 470 respectively. The combination of the electromagnetic coil assemblies 472 and permanent magnet ring 470 are similar in construction. The ferromagnetic rings 474 are attached to the stator portion 426 by suitable mounts, illustrated at 478. Thus, by varying the current supplied to the electromagnetic coil assemblies 472 and the resulting interaction with the permanent magnet ring 470, the disc 468 is movable axially thereby effecting axial movement of the cylinder 460 and the disc 466 on which the permanent magnet rings 454 are mounted. Accordingly, by varying the current to the electromagnet coil assemblies 472, the permanent magnet rings 454 may be moved axially toward and away from the permanent magnet rings 452.

The axial position of the rotor 406 is monitored by a probe, illustrated schematically at 480, which may, for example, be a Hall-effect device. Signals from the probe 480 are continually sent to a current controller circuit 482 via line 483, powered by a suitable power supply 484, which outputs current via lines 486 and 488 to the electromagnetic coil assemblies 472 respectively based on the signals of rotor position to effect movement of the rotor to the predetermined position, using principles commonly known to those of ordinary skill in the art to which this invention pertains. There is an attractive force between each pair of corresponding permanent magnet rings 452 and 454 across the gap 434. When the magnet rings 454 are moved in a direction axially away from magnet rings 452, the lessened or weakened flux or attraction therebetween will result in a lessened tendency of the rotor to also move in that direction. Thus, as viewed in FIG. 10, when the magnet rings 454 are moved to the right, the magnet rings 452 will be more free to move to the left. Conversely, when the magnet rings 454 are moved to the left, the magnet rings 452 will be urged more to move to the right.

The magnet rings 444 are mounted in a repulsive relation to the corresponding magnet rings 442. When a corresponding pair of magnet rings 442 and 444 are aligned, they are still unstable since an axial force on the rotor will cause the magnet ring 442 to move axially away from the corresponding magnet ring 444. In accordance with the present invention, the magnet rings 442 and 444 are mounted so that the magnet rings 444 on the rotor are shifted a little to the left (away from the radial bearing 450) to a predetermined position relative to the corresponding magnet rings 442 on the stator so that there will be continuously a greater or lesser amount of force acting to pull the rotor to the left (away from the radial bearing 450). The width of gap 434 or the distance between magnet rings 452 and 454 is initially selected to apply an equal force to the right to balance this force acting to pull the rotor to the left. If the rotor is pulled further to the left (past the predetermined position), this will be sensed by probe 480 which will so signal the current controller which will in turn vary the current to the electromagnetic coil assemblies 472 to interact magnetically with the permanent magnet 468 to effect movement of the magnet rings 454 to the left (toward magnet rings 452) thus increasing the attractive force therebetween to effect movement of the rotor back to the right to the predetermined position. If the rotor, when pulled to the right is pulled past the predetermined position, this will also be sensed by probe 480 which will so signal the current controller which will in turn vary the current to the electromagnetic coil assemblies 472 to interact magnetically with the permanent magnet 468 to effect movement of the magnet rings 454 to the right (away from magnet rings 452) thus decreasing the attractive force therebetween to allow movement of the rotor back to the left to the predetermined position. Thus, the rotor position is continuously monitored and the current to the electromagnetic coil assemblies 472 continuously varied as necessary to continually effect movement of the rotor to the predetermined axial position.

In order to contain the flow of fluid within the gaps 432, 434, and 436 so that it does not flow out into other spaces where it might stagnate, a suitable fluid impermeable flexible sheet 490 is suitably attached to suitably extend between disc 466 and the stator portion containing the motor stator coils 418, and another suitable fluid impermeable flexible sheet 492 is suitably attached to suitably extend between disc 466 and the stator portion 426.

It should be understood that, while the present invention has been described in detail herein, the invention can be embodied otherwise without departing from the principles thereof, and such other embodiments are meant to come within the scope of the present invention as defined by the appended claims.

What is claimed is:

1. A pump comprising a housing including a stator within said housing, an inlet means to said housing, and an outlet means to said housing, a motor including a rotor which is positioned to be interactive with said stator for rotation thereof, means attached to said rotor for forcing a fluid received from said inlet means through said outlet means, thrust bearing means comprising at least one pair of permanent magnet ring means including a magnet ring means on said rotor and a magnet ring means on said housing, said magnet ring means on said rotor and said magnet ring means on said housing facing each other on opposite sides of at least one radially extending gap between said housing and said rotor and oriented relative to each other to be attractive, means for sensing axial displacement of said rotor and effecting signals related thereto, and means responsive to the signals related to axial displacement of said rotor for moving said permanent magnet ring means on said housing axially relative to said permanent magnet ring means on said rotor.

2. A pump according to claim 1 wherein said rotor is shaped to have a bore extending axially therethrough and positioned to rotate about said stator so that said stator is received within the bore of said rotor.

3. A pump according to claim 1 further comprising at least one axially extending extension on each of said rotor and said stator and positioned to define an axially extending gap therebetween and journal bearing means comprising a first pair of axially polarized permanent magnet ring means on said rotor extension and said stator extension respectively on opposite sides of the axially extending gap, means for providing a repulsive relationship between said first magnet ring means, said repulsive relationship means comprising an orientation of said first magnet ring means so that a north pole on one of said first magnet ring means faces a north pole on an other of said first magnet ring means, and a second pair of axially polarized permanent magnet ring means on said rotor extension and said stator extension respectively on opposite sides of said axially extending gap, means for providing a repulsive relationship between said second magnet ring means, said repulsive relationship means comprising an orientation of said second magnet ring means so that a north pole on one of said second magnet ring means faces a north pole on an other of said second magnet ring means, said second magnet ring means disposed adjacent to said first magnet ring means respectively and having polarity in the opposite direction so that like poles on the first and second magnet ring means respectively are adjacent each other.

4. A pump according to claim 1 wherein said permanent magnet ring means is axially polarized.

5. A method of controlling rotor position comprising selecting a predetermined position axially of the rotor relative to a stator so that at least one permanent magnet ring means on the rotor faces in a repulsive relationship across an axially extending gap a respective permanent magnet ring means on the stator and is axially offset from an aligned position therewith, sensing movement of the rotor axially and effecting signals relating thereto, and moving axially, in response to the signals relating to movement of the rotor axially, at least one permanent magnet ring means on the stator which faces in an attractive relationship across a radially extending gap a respective permanent ring means on the rotor to move the rotor back to the predetermined position.

6. A pump comprising a housing, a motor including a stator and a rotor within the housing, an inlet means to said housing, an outlet means to said housing, means attached to said rotor for forcing a fluid received from said inlet means through said outlet means, said rotor having a central portion and a pair of axially extending extensions, said extensions disposed relative to said stator to define a pair of gaps between said extensions respectively and said stator, said central portion having a diameter which is greater than diameters of said extensions respectively and disposed relative to said stator to define a pair of radially extending gaps therebetween, and means for magnetically suspending said rotor in a non-contacting relation with said housing, said suspending means comprising journal bearing means for bearing said rotor and including interactive magnetic means on each of said rotor and said stator on opposite sides of each of the axially extending gaps, and active thrust bearing means for bearing said rotor, said journal bearing means for each of the axially extending gaps comprising a first pair of permanent magnet ring means on said rotor extension and said stator respectively on opposite sides of the respective axially extending gap, means for providing a repulsive relationship between said first magnet ring means, said repulsive relationship means comprising an orientation of said first magnet ring means so that a north pole on one of said first magnet ring means faces a north pole on an other of said first magnet ring means, said journal bearing means further comprising a second pair of permanent magnet ring means on said rotor extension and said stator respectively on opposite sides of the respective axially extending gap, means for providing a repulsive relationship between said second magnet ring means, said repulsive relationship means comprising an orientation of said second magnet ring means so that a north pole on one of said second magnet ring means faces a north pole on an other of said second magnet ring means, said second magnet ring means disposed adjacent to said first magnet ring means respectively and having polarity in the opposite direction so that like poles on the first and second magnet ring means respectively are adjacent each other, and wherein said thrust bearing means comprises permanent magnet ring means on said rotor adjacent at least two radially extending gaps between said rotor and said stator, and means comprising a pair of electromagnetic ring means on said stator adjacent said gaps respectively for magnetically interacting with said permanent magnet ring means for both rotating said rotor and maintaining axial position thereof, said pair of electromagnetic ring means being wound for magnetically interacting with said thrust bearing permanent magnet ring means for both rotating said rotor and maintaining axial position thereof.

7. A pump according to claim 6 wherein each of said first and second pairs of permanent magnet ring means is axially polarized.

8. A pump according to claim 6 wherein each of said axially extending gaps extends in a direction substantially parallel to a rotational axis of said rotor.

9. A pump according to claim 6 further comprising means responsive to axial velocity of said rotor for controlling said electromagnetic means for axially moving said rotor, said controlling means comprising means for producing axial velocity signals of said rotor, velocity feedback controller means responsive to the axial velocity signals for outputting signals to said electromagnetic means for seeking a position of zero force, and circuit means in communication with said controller means for applying an axial velocity to said rotor for self-starting said controller means.

10. A pump comprising a motor, a housing including a stator for said motor, an inlet means to said housing, an outlet means to said housing, a rotor for said motor, means attached to said rotor for forcing a fluid received from said inlet means through gaps between said rotor and said housing and then through said outlet means, and means for magnetically suspending said rotor in a non-contacting relation with said housing, said suspending means comprising an axially centrally disposed extension of said rotor and a pair of axially outer radially extending extensions of said rotor and a plurality of radially extending extensions of said housing which are interleaved with said rotor extensions to define a pair of centrally disposed and a pair of axially outer radially extending gaps respectively between said rotor and said housing, journal bearing means for bearing said rotor and including magnetic means on each of said rotor and said housing and disposed in interactive facing relationship on opposite sides of each of the axially outer radially extending gaps, and thrust bearing means for bearing said rotor and having interactive magnetic means which is disposed on both said rotor and said housing and which is disposed alongside the centrally disposed radially extending gaps, and said motor having a bearing span which is at least about 2½ times greater than an average radius of distributed force.

11. A pump according to claim 10 wherein said journal bearing means comprises at least one first pair of permanent magnet ring means on said rotor and said housing respectively on opposite sides of said first radially extending gap and concentric with a rotor rotational axis, means for providing an attractive relationship between said first magnet ring means, said attractive relationship means comprising an orientation of said first magnet ring means so that a north pole on one of said first magnet ring means faces a south pole on an other of said first magnet ring means, and at least one second pair of permanent magnet ring means on said rotor and said housing respectively on opposite sides of said first radially extending gap and concentric with the rotor rotational axis, means for providing an attractive relationship between said second magnet ring means, said attractive relationship means comprising an orientation of said second magnet ring means so that a north pole on one of said second magnet ring means faces a south pole on an other of said second magnet ring means, said second magnet ring means disposed radially inwardly of and adjacent to said first magnet ring means respectively, and the pole of said second magnet ring means on rotor which faces said second magnet ring means on said housing being of a polarity which is opposite the polarity of the pole of said first magnet ring means on said rotor which faces said first magnet ring means on said housing.

12. A pump according to claim 11 wherein each of said first and second pairs of permanent magnet ring means is axially polarized.

13. A pump according to claim 10 wherein said thrust bearing means comprises at least one permanent magnet means on said rotor and between and alongside a pair of said second radially extending gap and a pair of electromagnetic means on said housing and alongside said pair of second radially extending gaps respectively for controlling magnetic force between said electromagnetic means and said permanent magnet means for thereby controlling axial position of said rotor.

14. A pump according to claim 10 wherein said rotor is shaped to have a bore extending axially therethrough and positioned to rotate about said stator so that said stator is received within the bore of said rotor.

15. A pump according to claim 10 further comprising means responsive to axial velocity of said rotor for controlling said electromagnetic means for axially moving said rotor, said controlling means comprising means for producing axial velocity signals of said rotor, velocity feedback controller means responsive to the axial velocity signals for outputting signals to said electromagnetic means for seeking a position of zero force, and circuit means in communication with said controller means for applying an axial velocity to said rotor for self-starting said controller means.

16. A pump comprising a housing including a stator, an inlet means to said housing, an outlet means to said housing, a rotor shaped to have a bore extending axially therethrough and positioned to rotate about said stator so that said stator is received within the bore of said rotor, means attached to said rotor for forcing a fluid received from said inlet means through gaps between said rotor and said housing and then through said outlet means, and means for magnetically suspending said rotor in a non-contacting relation with said housing, said suspending means comprising at least one radially extending extension on said rotor which defines with said housing a plurality of radially extending gaps between said at least one rotor extension and said housing, journal bearing means for bearing said rotor and including magnetic means on each of said rotor and said housing and disposed in interactive facing relationship on opposite sides of at least a first of the radially extending gaps, and thrust bearing means for bearing said rotor and including magnetic means on each of said rotor and said housing and disposed in interactive facing relationship on opposite sides of at least a second of the radially extending gaps.

17. A pump according to claim 16 wherein said motor has a bearing span which is at least about 2½ times greater than an average radius of distributed force.

18. A pump according to claim 16 wherein the pump is implantable in a body, the fluid being blood.

19. A pump according to claim 16 wherein each of said gaps extends in a direction substantially normal to a rotational axis of said rotor.

20. A pump according to claim 16 comprising a plurality of said radial extension of said rotor and a plurality of radial extensions of said housing which are interleaved with said rotor extensions.

21. A pump according to claim 16 comprising a central and a pair of axially outer ones of said radial extension of said rotor and a pair of radial extensions of said housing which are interleaved with said rotor extensions to define a pair of axially inner radially extending gaps and a pair of axially outer radially extending gaps.

22. A pump according to claim 21 wherein said journal bearing means is disposed alongside said axially outer radially extending gaps, and said thrust bearing means is disposed alongside said axially inner radially extending gaps.

23. A pump according to claim 16 wherein said journal bearing means comprises at least one first pair of axially polarized permanent magnet ring means on said rotor and said housing respectively on opposite sides of said first radially extending gap and concentric with a rotor rotational axis, means for providing an attractive relationship between said first magnet ring means, said attractive relationship means comprising an orientation of said first magnet ring means so that a north pole on one of said first magnet ring means faces a south pole on an other of said first magnet ring means, and at least one second pair of axially polarized permanent magnet ring means on said rotor and said housing respectively on opposite sides of said first radially extending gap and concentric with the rotor rotational axis, means for providing an attractive relationship between said second magnet ring means, said attractive relationship means comprising an orientation of said second magnet ring means so that a north pole on one of said second magnet ring means faces a south pole on an other of said second magnet ring means, said second magnet ring means disposed radially inwardly of and adjacent to said first magnet ring means respectively, and the pole of said second magnet ring means on said rotor which faces said second magnet ring means on said housing being of a polarity which is opposite the polarity of the pole of said first magnet ring means on said rotor which faces said first magnet ring means on said housing.

24. A pump according to claim 23 wherein said thrust bearing means comprises at least one permanent magnet means on said rotor and between and alongside a pair of said second radially extending gap and a pair of electromagnetic means on said housing and alongside said pair of second radially extending gaps respectively for controlling magnetic force between said electromagnetic means and said permanent magnet means for thereby controlling axial position of said rotor.

25. A pump according to claim 16 wherein said thrust bearing means comprises at least one permanent magnet means on said rotor and between and alongside a pair of said second radially extending gap and a pair of electromagnetic means on said housing and alongside said pair of second radially extending gaps respectively for controlling magnetic force between said electromagnetic means and said permanent magnet means for thereby controlling axial position of said rotor, means responsive to axial velocity of said rotor for controlling said electromagnetic means for axially moving said rotor, said controlling means comprising means for producing axial velocity signals of said rotor, velocity feedback controller means responsive to the axial velocity signals for outputting signals to said electromagnetic means for seeking a position of zero force, and circuit means in communication with said controller means for applying an axial velocity to said rotor for self-starting said controller means.

26. A pump according to claim 25 further comprising means responsive to axial velocity of said rotor for controlling said electromagnetic means for axially moving said rotor, said controlling means comprising means for producing axial velocity signals of said rotor, velocity feedback controller means responsive to the axial velocity signals for outputting signals to said electromagnetic means for seeking a position of zero force, and circuit means in communication with said controller means for applying an axial velocity to said rotor for self-starting said controller means.

\* \* \* \* \*